United States Patent
Hadvary et al.

(10) Patent No.: US 10,149,974 B2
(45) Date of Patent: Dec. 11, 2018

(54) SUB-EPIDERMAL ELECTRIC WARNING DEVICE

(71) Applicant: PharmaSens AG, Biel-Benken (CH)

(72) Inventors: Paul Hadvary, Biel-Benken (CH);
Hansjorg Tschirky, Sissach (CH);
Rudolf Dinger, Saint-Aubin (CH);
Jean-Pierre Michot, Basel (CH)

(73) Assignee: PHARMASENS AG, Benken (CH)

( * ) Notice: Subject to any disclaimer, the term of this patent is extended or adjusted under 35 U.S.C. 154(b) by 819 days.

(21) Appl. No.: 14/408,075

(22) PCT Filed: Jun. 12, 2013

(86) PCT No.: PCT/EP2013/062180
§ 371 (c)(1),
(2) Date: Dec. 15, 2014

(87) PCT Pub. No.: WO2014/001091
PCT Pub. Date: Jan. 3, 2014

(65) Prior Publication Data
US 2015/0174401 A1 Jun. 25, 2015

(30) Foreign Application Priority Data
Jun. 25, 2012 (EP) .................................... 12173390

(51) Int. Cl.
*A61M 5/00* (2006.01)
*A61N 1/36* (2006.01)
(Continued)

(52) U.S. Cl.
CPC ...... *A61N 1/36017* (2013.01); *A61B 5/14532* (2013.01); *A61B 5/4839* (2013.01); *A61B 5/688* (2013.01); *A61B 5/6833* (2013.01); *A61B 5/6848* (2013.01); *A61B 5/7455* (2013.01); *A61M 5/14244* (2013.01); *A61M 5/14248* (2013.01); *A61M 5/16831* (2013.01); *A61M 5/1723* (2013.01); *A61N 1/0502* (2013.01); *A61N 1/32* (2013.01); *A61B 2562/242* (2013.01); *A61M 2005/14252* (2013.01); *A61M 2205/18* (2013.01); *A61M 2205/702* (2013.01)

(58) Field of Classification Search
CPC ............ A61N 1/36017; A61B 5/14532; A61B 5/4839; A61B 5/6833
USPC ........................................................ 604/111
See application file for complete search history.

(56) References Cited

U.S. PATENT DOCUMENTS 5,931,814 A 8/1999 Alex et al.
6,175,763 B1 * 1/2001 Sorenson ................. A61N 1/30
604/20
(Continued)

FOREIGN PATENT DOCUMENTS

EP   2436311 A1    4/2012
EP   2438938 A1    4/2012
WO   WO 02/15778 A1   2/2002

*Primary Examiner* — Phillip Gray
(74) *Attorney, Agent, or Firm* — Xsensus LLP

(57) ABSTRACT

A sub-epidermal electric warning device has electrodes penetrating through the patient's epidermis and bipolar electric warning signals are transmitted to the sub-epidermal tissue by these electrodes. A device for surveillance of vital signs, analyte levels, or treatment parameters is using a sub-epidermal electric warning device for notifying the patient in situations requiring intervention.

17 Claims, 4 Drawing Sheets

(51) Int. Cl.
*A61B 5/00* (2006.01)
*A61B 5/145* (2006.01)
*A61M 5/142* (2006.01)
*A61N 1/05* (2006.01)
*A61M 5/172* (2006.01)
*A61N 1/32* (2006.01)
*A61M 5/168* (2006.01)

(56) References Cited

U.S. PATENT DOCUMENTS

| | | |
|---|---|---|
| 6,685,675 B1 | 2/2004 | Hadvary et al. |
| 2008/0021519 A1 | 1/2008 | De Geest et al. |
| 2008/0027296 A1 | 1/2008 | Hadvary et al. |
| 2008/0086041 A1 | 4/2008 | Heller et al. |
| 2011/0196256 A1* | 8/2011 | Inui ................ A61B 5/4824 |
| | | 600/554 |

* cited by examiner

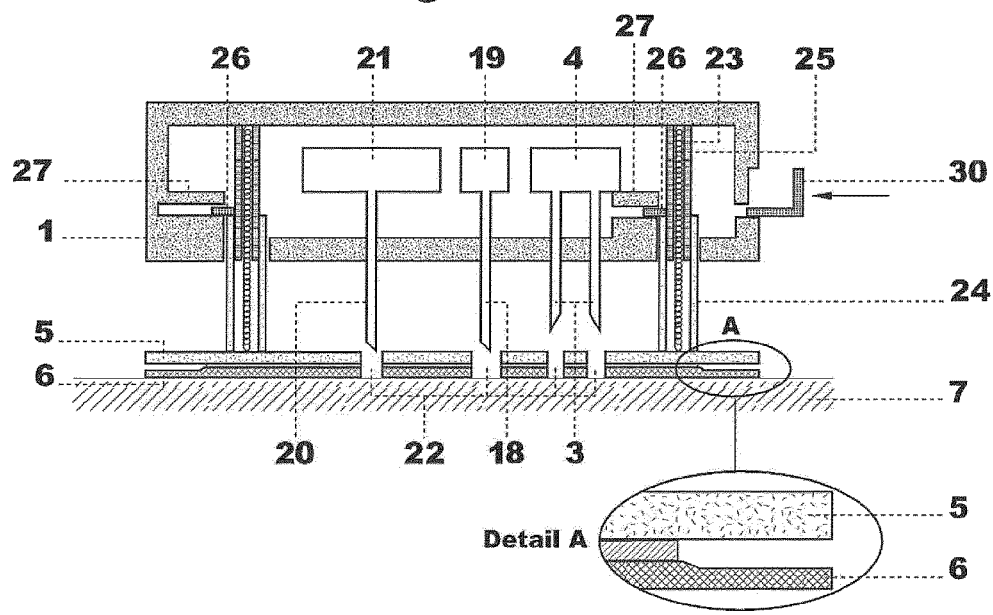
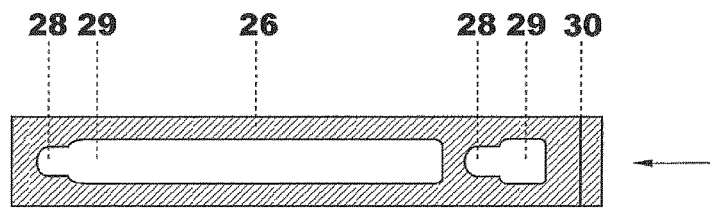
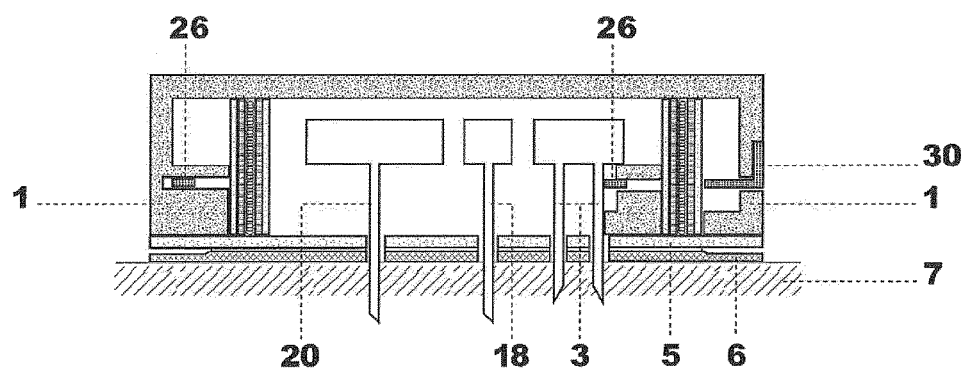

SUB-EPIDERMAL ELECTRIC WARNING DEVICE

The present invention is related with warning devices for patients under continuous surveillance and/or treatment.

One major field of application for this type of electric warning devices is the notification or alarming of the patient in cases of abnormal values for physiologic or analytical parameters or failure of treatment devices requiring an intervention. This occurs for instance in diagnostic devices if the patients situation needs particular care (e.g. administration of medication), and with therapeutic devices it is extremely important to be able to alert the patient if the device is not operating within the specified limits.

Proper treatment of many patient conditions depends on continuous surveillance. With the availability of ambulatory devices for continuous surveillance of vital signs such as e.g. heart rate or of analytes such as e.g. glucose, or for the delivery of medication, such as e.g. insulin a robust warning device for dangerous conditions has to be available. Transmitting optical or acoustic notification or alarm signals to the patient is well known for such indications. Currently available warning devices transmit mainly visible, audible or vibration signals and are therefore heavily dependent on the awareness and attention state of the user, and recognition is problematic e.g. during sleep or in the presence of environmental disturbing factors, e.g. during watching films, listening to music or news, or during car driving.

To overcome the limitations of the well-known optical, acoustic or vibrating alarm systems for medical devices, electric alarm systems have been suggested for medical applications. It is well known, that sensatory nerves react to electric stimuli. Electric warning signals are different from normal environmental signals and therefore less prone to become masked under unfavorable conditions. Transmitting electric alarm signals is well known through skin-attached contacts as described e.g. in US20088021519A, but due to the highly isolating epidermal layer of the skin, a high voltage and a high current has to be applied for a reliable signaling, according to this disclosure in the order of 75 Volt and about 30 mA, representing a potential danger to the patient. In addition, the insulating capacity of the epidermis is highly variable, and therefore the alarm signal is difficult to dose, especially since the useful window between safe recognition of the signal and a very disagreeable shock is narrow. Iontophoretic channels for delivering an electrical current to provide a tactile stimulus as disclosed e.g. in WO 02/15778A1 do not significantly improve the need for high voltages and currents and are also subject to a high level of variability.

In contrast to electrodes transmitting the signal placed onto the skin requiring relatively high voltages for a sensatory stimulus, a clear recognition is possible with low voltages if the insulation by the stratum corneum is bypassed, well known e.g. by the experience that pressing the electrodes of a 4.5V battery against the tongue creates a clear sensation.

Similarly, the drawback of the need for high voltages with electrodes placed on the skin can be overcome by placing the electrodes underneath the epidermal layer of the skin. For example US 2008/0086041 A1, mentions among a list of other alarm systems an electric alarm by placing the electrodes on an indwelling glucose sensor and producing a mild shock with a current of 0.1 to 1 mA applying a potential between the conductive traces of typically 1 to 10 Volts; the technical implementation of the alarm system is not further described.

An electric alarm system would be very reliable allowing alerting a patient even in difficult environmental conditions or when the person is distracted by his professional or other activities or during sleep. On the other hand, electric stimulation can have adverse effects. Since Luigi Galvani's experiment on frog legs in 1771 it is known that a small electric current pulse allows to stimulate the nerves or directly the muscles of the human body and the technology is used since years in devices for heart stimulation ("pace makers"), more recently also for the stimulation of specific muscles after surgery (in the back) etc. The purpose of these applications is to stimulate specific muscles; the electrodes are carefully placed to avoid undesirable stimulation of the sensatory nerves which would cause the uncomfortable feeling of electric shocks or even pain to the patient.

The aim of the present invention is to provide an electric warning device which avoids the disadvantages of the state of the art devices and is user-friendly and safe, achieving with a small current pulse of low voltage a strong sensatory nerve stimulus without fading over short time, having minimal intra- and inter-individual variability, avoiding undesirable muscle stimulation, and without the uncomfortable feeling of electric shocks or even pain to the patient.

According to the invention this is achieved in that electrodes are placed into the sub-epidermal tissue, penetrating through the insulating epidermis layer of the skin and delivering the electric signal directly to the sub-epidermal tissue, thus avoiding the need for high voltages and currents and strongly reducing inter-individual variability. Importantly, to achieve this goal, the electrical stimulus of the current invention creates bipolar current pulses of alternating positive and negative polarity, maximizing the window between clear sensation and uncomfortable feeling of electric shocks or even pain, and avoiding a rapid decline of the sensational signal.

For this use the electric warning device is usually equipped with both a contact surface for attaching to a user's skin and two electrodes penetrating the user's epidermis and transmitting the electric stimulus creating bipolar current pulses of alternating positive and negative polarity to the underlying tissue.

When used herein, the following definitions define the stated term

Adhesive layer for temporary wearing on the skin is made of materials with strong adhesive properties, stretch ability and minimal allergenicity. This adhesive layer is fixed on the skin attachment surface of the device preferentially by a reduced surface in comparison to the surface of the adhesive layer securing attachment to the skin. This can be accomplished e.g. by an adhesive layer extending beyond the skin attachment surface. Alternatively, this can also be achieved by using a shape for the adhesive layer similar to or only slightly larger than the skin attachment surface of the device but by fixing the adhesive layer to the skin attachment surface in such a way that an outer rim is not fixed together, allowing this flexible outer rim of the adhesive layer to adapt to the flexibility of the skin, especially to changes under tearing conditions. Such a design is described in EP0825882 for a medical device with a rigid base.

Control elements for the generation of the electric warning signal include the electronics for the generation of the signal and communication means with elements generating input signals relevant for triggering the actuation of the electric warning signal, as well as for terminating signaling upon confirmation of signal perception by the user.

Electrodes penetrating through the patient's epidermis into the skin for transmitting electric warning signals are preferentially miniaturized needles, below 0.3 mm in diameter of stainless steal or of other implantable materials conducting electrical current. It was found that subcutaneous placing of the electrodes leads to clear and safe signal recognition at low voltage of less than 9V with resulting currents below 1 mA, thus avoiding any electrical risk to the patient. Further, by penetrating the insulating skin barrier the inter- and intra-patient variability for voltage-dependent signal recognition becomes small and the margin between safe recognition of the signal and a disagreeable shock or pain is sufficiently broad for reaching a safe signaling without disturbance to patient comfort.

Electric warning signal consists preferentially of small pulses of 5 to 20 msec duration which are transmitted at preferentially 1 Hz frequency. A rapid switching results in very short current pulses with peaks below 1 msec, further reducing exposure of the user.

Following tests with different suitable electrical circuits generating electrical pulses it was surprisingly found that an electric circuitry with rapid switch-on of a DC source and thereafter rapidly switching to the negative pole of this DC source, results in clear sensatory recognition at lower voltage and does not lead to a rapid fading of the signal perception, in contrary to pulses, e.g. obtained by discharge of a condenser, thus expanding the range between safe and comfortable signal recognition and disagreeable pain sensation. This surprising finding of a clear difference between circuitries applying basically the similar current pulse, and the largely improved sensatory recognition with a circuitry not of prime choice for such a device led to analysis of the current pulse obtained using the above mentioned switching the electrodes from the positive to the negative poles of a DC source. It was found, that alternatively positive and negative current pulses were generated, having peaks of a positive polarity at switch-on of the DC source and of negative polarity at switch-off and rapid switching to the negative pole of this DC source. This surprising finding of a largely improved sensatory recognition resulting from pulse pairs of opposite polarity forms the basis of the current invention.

The shape of the current tracings leading to this important sensatory improvement shows a behavior known in electronics from a series circuit of a resistor and a capacitor. Thus, it is possible to design a number of circuits resulting in similar current pulse pairs consisting of a positive and a negative pulse. The positive and negative pulses follow each other preferentially within 1 to 100 milliseconds. The electrical pulse pairs are delivered preferentially with a clock frequency of 0.2 to 5 Hz, more preferably of 1 Hz and increasing intensity over time: the electrical signaling begins with low-voltage pulses and increases in small steps until the user confirms the perception of the signal, e.g. by pressing a button. The electric warning signal can be delivered with different rhythm for different types of warning messages.

Functional package is designed to hold the device by a releasable coupling mechanism and has a peel-off cap to protect sterility. The functional package has also a rim element allowing, after removal of the peel-off cap, the correct attachment of the rim of the adhesive layer which extends over the skin attachment surface. Firm pressing the rim of the adhesive layer all-around against the skin is important for securing long-term persisting attachment to the skin. Further, the functional package protects the release and actuation element against premature, unintended operation: the release and actuation element can be actuated only following attachment of the device to the skin and removal of the functional package. In addition, in case that the device is composed of a reusable part and a disposable part, the functional package can have features facilitating and securing correct assembly and disassembly.

Insertion means for sub-epidermal insertion of the electrodes into the skin is preferentially not shooting the electrodes into the skin but pulling the skin attached by an adhesive, against the tip of the electrode needles. Such a mechanism of skin insertion is simple and reliable allowing mounting the electrodes fixedly, protruding from the bottom of the device casing. In addition it allows together with the electrodes the simultaneous subcutaneous placement of sensors and/or cannulas for delivery of fluid.

Insertion means pulling the skin attached by an adhesive layer towards the electrodes are configured in such a way that in the ready-to-use position the skin is kept away from contacting the tip of the electrodes which are fixedly positioned by the bottom of the device casing and, upon activation, the skin is pulled towards the tip of the electrodes with high velocity, effecting piercing of the skin and sub-epidermal insertion of the electrodes.

In a preferred embodiment, the insertion means comprises a skin attachment surface coated with an adhesive layer for securing attachment to the skin and having holes or recesses allowing the passage of the electrodes. Preferentially, the retraction mechanism of the skin attachment surface comprises a spring-type mechanism pulling the skin attachment surface together with the attached skin towards the tip of the electrodes with high velocity. In the ready-to-use position, withholding means are keeping the retraction mechanism pre-stressed such that the tip of the electrodes is concealed by the skin attachment surface and prevented to contact the skin. A release and actuation element, preferentially comprising a linear or circular sliding bold mechanism, is releasing the blockage of the retraction mechanism and actuating the control elements. The withholding means are constructed preferentially in such a way that upon release they guide the movement of the skin attachment surface towards the bottom of the device casing with the fixedly positioned, protruding electrodes.

The skin attachment surface can be a rigid plate with a retraction mechanism configured such that it keeps the rigid skin attachment plate and the bottom of the device casing parallel to each-other in the ready-to-use position and throughout retraction of the skin attachment plate towards the bottom of the device casing.

Alternatively, the skin attachment surface can be a flexible, segmented surface being attached to the bottom of the device casing at its periphery, and the retraction mechanism being configured such that in the ready-to-use position it stretches the central part of the contact surface away from the bottom of the device casing, forcing the attachment surface to form a cup or a gable. The retraction mechanism of the flexible contact surface can make use of the springy elasticity of this surface for a rapid movement by relaxation from an enforced tense position.

Such preferred skin insertion mechanisms pulling the skin against the tip of the electrodes allow also, in parallel, the insertion of other fixedly positioned needle-type functional elements, like sensors and cannulas into the subcutaneous tissue.

Means to generate an electric warning signal which is transmitted to the sub-epidermal tissue by the electrodes are electrical circuits generating pulses of current of defined voltage and duration. They include control elements receiving and processing input signals.

Pump system for subcutaneous fluid injection can comprise any type of pump well known in prior art having a subcutaneously placed cannula for fluid delivery. The control electronics of the pump system is preferably configured in such a way that in case of functional abnormalities of the pump system it transmits input signals to the control elements for the generation of the electric warning signal.

Sensor system senses physiological parameters of the user. These physiological parameters can be detected and measured either without or with subcutaneously inserted sensors, e.g. heart rate, oxygen saturation, or subcutaneous analyte concentrations, respectively. Sensors systems have an active sensor which provides some signal (e.g. electrochemical, optic, sonar, thermometric, surface plasmon resonance, piezoelectric or magnetic) according to the value of the physiological parameter or the concentration of the analyte. Sensors can be located within the device or be directly exposed to the subcutaneous tissue. The control electronics of the sensor is preferably configured in such a way that in case of abnormal values measured by the sensor it transmits input signals to the control elements for the generation of an electric warning signal. Sensors are preferentially placed into the skin remotely from the electrodes for transmitting electric warning signals to avoid interferences or damage of the sensors by the electric warning signals.

Sliding bolt mechanisms consists of elements which display a closed or open state, for example a solid surface or a hole, upon a circular or linear movement. The movement of the slide mechanism is actuated manually or is driven for example by a spring and actuated by a release element, for example through pressing a button or handle, or through a minimal turning movement. As part of the release and actuation element, movement of the sliding bolt mechanism from the ready-to-use position to the operation mode is actuating a rapid release of the blockage of the retraction mechanism and actuating the control elements of the device.

In the following, preferred embodiments of the invention are described with reference to the accompanying drawings in which FIG. 1 is a diagrammatic sectional view of a sub-epidermal electric warning device with insertion means for sub-epidermal insertion of the electrodes into the skin according to one embodiment of the invention. FIG. 1A shows the device in the ready-to-use mode, and FIG. 1B in the operation mode.

FIG. 4 is a diagrammatic sectional view of a sub-epidermal electric warning device further comprising a pump and a sensor system, with insertion means for subcutaneous insertion of the electrodes, a fluid delivery cannula and a sensor in parallel into the skin according to an alternative embodiment of the invention. FIG. 4A shows the device in the ready-to-use mode, FIG. 4B a detail of a sliding bold mechanism releasing the blockage of the retraction mechanism, and FIG. 4C the device in the operation mode.

FIG. 1 shows a diagrammatic sectional view of a sub-epidermal electric warning device with insertion means for sub-epidermal insertion of the electrodes into the skin according to one embodiment of the invention. Such a skin insertion mechanism allows precise sub-epidermal positioning of thin electrodes, preferentially having a diameter below 0.3 mm, with fixed connections to control elements generating the electric warning signal.

Figure 1A:
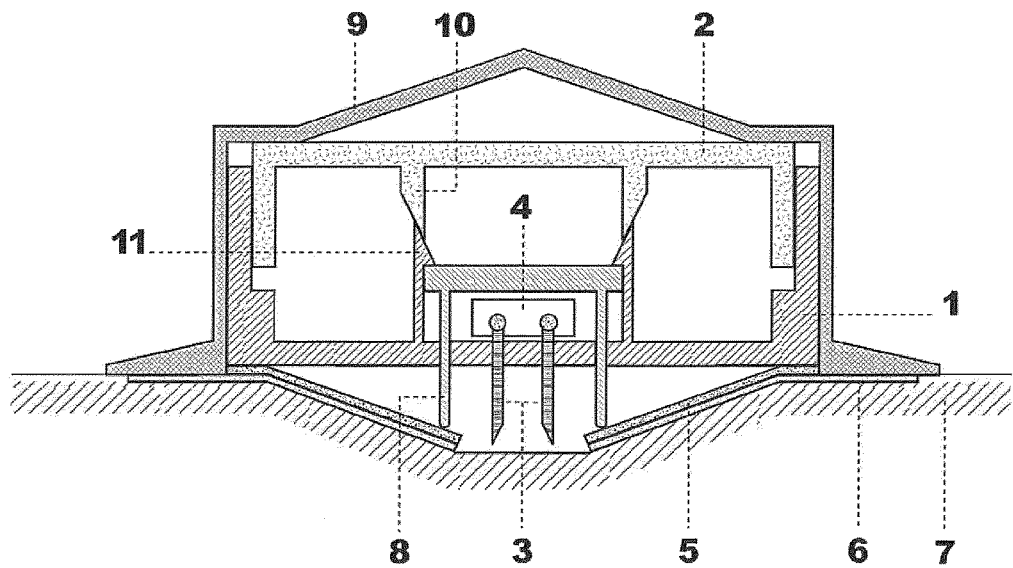

FIG. 1A shows the device in the ready-to-use mode.

A casing 1 has preferentially a circular or oval footprint with a cover 2, which can serve in this embodiment also as part of the release and actuation element. Electrodes 3 are rigidly positioned and protruding the bottom of the casing, being fixedly connected to control elements 4 generating an electric warning signal. A flexible skin attachment surface 5 is fixed along its periphery to the bottom of the casing and is coated with an adhesive layer 6 for secure attachment to a patient's skin 7.

The flexible skin attachment surface 5 has a radial segmentation, preferably into five to eight segments with spacing between them, forming a cone upon central bending or alternatively it consists of two segments with a diagonal slit, forming a gable upon bending. The segments are attached to the circumference of the casing by springy hinge regions and are in addition preferably made of a flexible material. The skin attachment surface has a central opening or a diagonal slit, respectively, and allows passage of the electrodes.

In the ready-to-use mode the skin attachment surface 5 is centrally bent away from the bottom of the casing by withholding means 8, against the pressure of the springy hinge regions of the skin attachment surface. Thus, the central cone or gable projects beyond the tip of the electrodes 3 and holds the skin away from the tip when the device is placed on a suitable body area, preferably the abdomen, the thigh, the upper or the forearm, and by gentle pressing is attached by means of the adhesive layer 6. In this example, the adhesive layer 6 has a larger circumference than the bottom of the device casing 1 and a functional package 9 has an outer rim pressing the circumference of the adhesive layer against the skin, ensuring firm attachment all-over.

The adhesive layer 6 for securing the device to the patient's skin is composed of three parts: glue for fixing to the flexible skin attachment surface, a textile providing the necessary flexibility and glue for fixing onto the skin. Suitable materials with low allergenicity potential are commercially available.

Figure 1B:
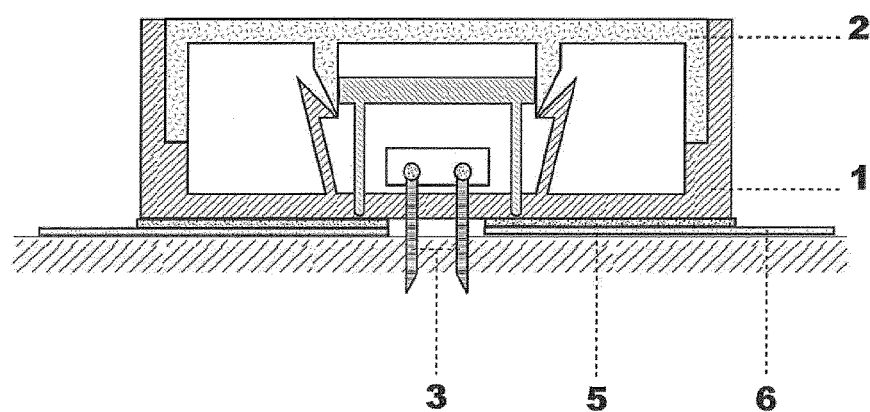

Upon fixing the device in the ready-to-use position to the skin, the functional package 9 protecting against unintended activation of the device can be removed, e.g. by a slight turn to disengage from the casing, giving access to the cover 2 which is designed as a release and actuation button in this embodiment. For this purpose the cover 2 has wedge-shaped elements 10 protruding downwards from the inner flat surface of cover 2. The slant surfaces of the wedge-shaped elements are contacting similarly slant surfaces of hooks 11 which are protruding upwards from the bottom of casing 1. By pressing the cover 2 the wedge-shaped elements 10 are bending the hooks 11 radially, thus disengaging the withholding means 8. This releases the withholding means 8 and the stretched spring-type skin attachment surface 5 shoots into the relaxed, flat position pulling the attached skin 7 against the bottom of the casing with the rigidly held electrodes. This effects the insertion of the electrodes 3 into the skin, resulting in the configuration depicted in FIG. 1B, showing the device in operation mode following insertion of the electrodes into the skin.

Figure 2A:
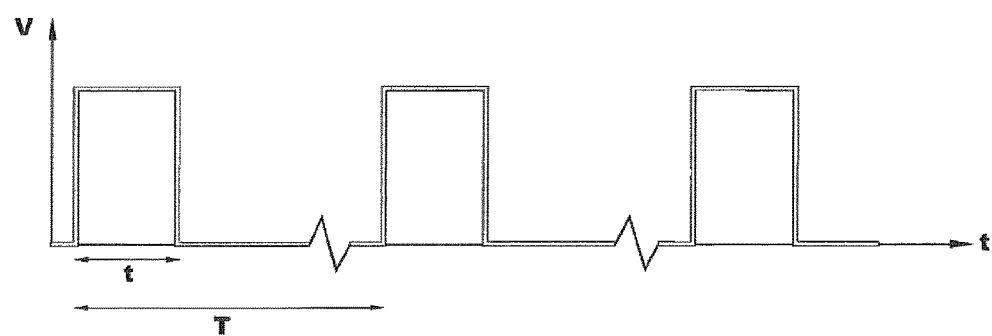
FIG. 2 is a schematic representation of the warning signal having alternating current pulses of opposite polarity.
Figure 2B:
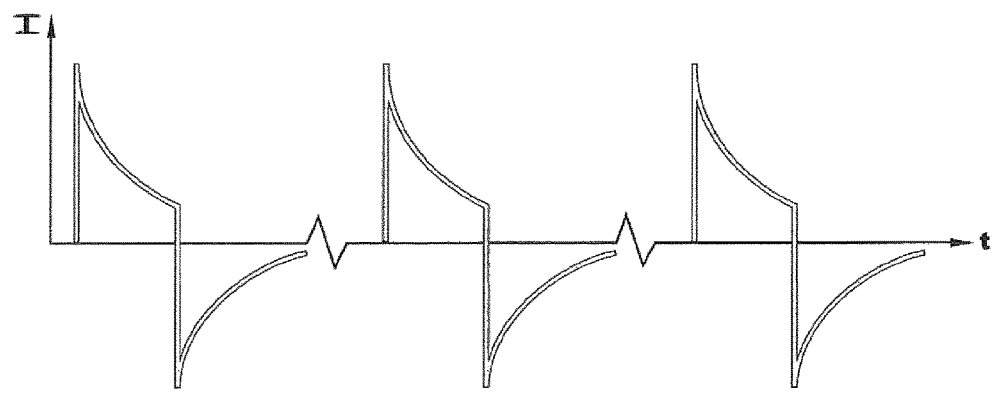

FIG. 2 is a schematic representation of a warning signal having alternating current pulses of opposite polarity according to the current invention. In FIG. 2A, as an example, the voltage diagram applied to the electrodes with an electric circuitry with rapid switch-on of a DC source and thereafter rapidly switching to the negative pole of this DC source is shown and in FIG. 2B the resulting current profile. Preferentially, voltage pulses of 2 to less than 9 Volts and of a duration [t] of 1 to 100 milliseconds are applied, and the bipolar pulse pairs are repeated separated by 0.2 to 5 seconds. Most preferably, the pulses are repetitively applied for about 5 msec each. The body's sensitivity does not increase any more if longer pulses are applied; it however substantially decreases with pulses of less than 1 msec duration. Voltage pulses as shown in FIG. 2A are applied repeatedly after a period of time [T] each. For best recognition T is of the order of 1 second. Shorter periods of T do not increase the alarm signal recognition, but the signal becomes increasingly uncomfortable and longer periods of T lead to less well recognized signals.

FIG. 2B shows the observed current signal obtained with a suitable circuitry generating current pulses of opposite polarity. This can be achieved e.g. by a rapid switch-on of a DC voltage followed by a rapid switch-off against ground. The relatively high salt content in the human body fluid leads to the body fluid being a good electrical conductor and suggests the body to be a resistive load. One would expect therefore to see a current signal of rectangular shape of the duration of the voltage signal t and of current amplitude $I_0$, $I_0$ being equal to $V_0/R$. FIG. 2B shows however, that this is not the case. The current takes an initial value $I_0$ and then decreases steadily until the voltage pulse stops. This is the typical current signal known in electronics as a capacitor-resistor (CR) series circuit. The experimental data obtained with the described example of a circuitry with a DC source suggest that the body is not a purely resistive load for the voltage signal applied by the device, but shows also a strongly capacitive behavior. This result in a current signal characteristic for a capacitor charge and discharge phenomenon: at the positive slope of the voltage signal the capacitor is charged resulting in a positive current pulse, inversely at the negative slope of the voltage signal the capacitor is discharged causing the negative current pulse as shown in the figure. If the pulse duration t is of the order of the decay time of the current signal, the current is not yet zero when the voltage pulse is switched off and the negative current peak resulting from switching to the negative pole of the DC source is slightly smaller than the positive one as shown in FIG. 2B. The period time T is in any case much longer than the decay time of the current pulse, therefore at the start of the voltage pulse, the current is practically zero.

It is well known (e.g. from safety considerations on the electric power grid) that the human body is sensitive to the electric current signal rather than to the voltage applied. Surprisingly, it was found that a circuitry resulting in bipolar current pulses as shown in FIG. 2B gives a more effective stimulus to the nerves than current pulses having always the same polarity resulting e.g. from a periodic discharge of a capacitor. In particular it has been found that signals with bipolar pulses are recognized at lower voltage than pulses of unchanged polarity, and that the body gets rapidly used to signals of constant polarity, whereas there is little or no fading of the recognition sensitivity with bipolar pulses. In addition these effects increase the window between clear signal recognition and uncomfortable electric shock or even pain encountered if a higher voltage is applied.

The threshold for clear recognition depends on individual sensitivity, location of the device on the body, and general awareness/distraction. Therefore, preferentially the warning signaling starts with pulses of low voltage and the voltage is then gradually increased until the user clearly recognizes and confirms the warning signal, resulting in optimal safety and user comfort.

Figure 3:
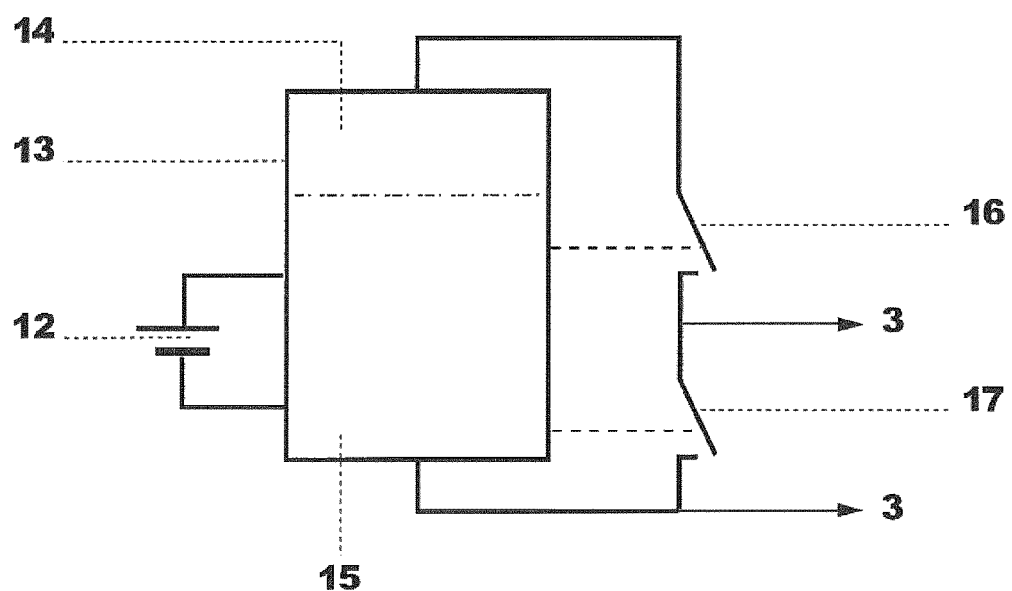
FIG. 3 is a schematic representation of a typical circuitry generating warning signals.

FIG. 3 shows a schematic representation of a typical circuitry generating bipolar, alternatively positive and negative current pulses as warning signal as schematically depicted in FIG. 2. A power supply, e.g. a battery 12 is supplying the power to a control unit 13 containing a DC-DC converter 14 and a pulse generator 15. Electronic switches 16 and 17, operated by the control unit, are alternatively switched on and off, thus creating the voltage pulses shown in FIG. 2A. Electronic circuits such as shown in FIG. 3 but also many alternative circuits delivering bipolar electrical warning signals as shown in FIG. 2A are well known to the people skilled in the art.

FIG. 4 is a diagrammatic sectional view of a device containing a sub-epidermal electric warning system 3, 4, a pump system 20, 21 for fluid injection and a sensor system 19 with a subcutaneously implanted sensor 18. The insertion means into the skin according to an alternative embodiment of the invention described in this figure allows simultaneous insertion of the electrodes, a fluid delivery cannula as delivery outlet of the pump system, and a sensor into the skin. Complex therapeutic systems, such as closed-loop systems e.g. for diabetes care, with an insulin delivery pump under the feed-back control of a glucose sensor need a high level of function and outcome control. With the electric warning system of the current invention integrated in such a therapeutic device the patient can be reliably notified in case any functional or measured abnormalities occur, requiring action by the patient.

FIG. 4A shows the device in the ready-to-use mode pressed against the skin. The skin attachment surface 5 is in this alternative embodiment a rigid plate and the adhesive layer 6 is ensuring a firm attachment to the skin 7. Whereas in the embodiment depicted in FIG. 1 the adhesive layer 6 for attachment to the skin has a larger surface than the skin attachment plate 5, in the embodiment shown in this figure both have a similar surface but the adhesive layer 6 is fixed on the skin attachment plate 5 by a reduced surface, leaving an outer rim free, as shown in Detail A. Both designs prevent unintended detachment from the skin, allowing the adhesive layer at its peripheral rim to adapt flexibly to the form and movements of the skin surface.

The electrodes 3 of the electric warning system 4, the subcutaneously implantable sensor 18 of the sensor system 19 and the cannula 20 of the pump system 21 are rigidly positioned and protruding the bottom of the device casing 1 and, in addition, are fixedly connected to the control elements 4, the sensor system 19, and the pump system 21, respectively.

The skin attachment plate 5 coated with the adhesive layer 6 has holes 22 opposing the tip of the electrodes 3, the sensor 18 and the cannula 20. In this embodiment of the invention, the skin attachment plate 5 and the bottom of the device casing 1 are movably connected by a spring-type retraction mechanism comprising a telescopic guide ways with an inner tube 23 fixed to the upper part of the casing of the device. Tube 23 can slide within an outer tube 24 fixed to the skin attachment plate to ensure a smooth and axially well-defined movement. A pull-spring 25 hauled between the skin attachment plate 5 and the housing is situated inside the inner tube 23. Withholding means are constructed as a sliding bolt mechanism consisting of a movable plate 26 sliding within a slot 27. In the ready-to-use mode the outer tube 24 of the guide ways attached to the skin attachment plate 5, is withhold against the pull of the spring 25 in such a way that the skin attachment plate is sufficiently spread away from the bottom of the casing 1 to conceal the electrodes 3, the sensor 18 and the cannula 20 protruding from the bottom of the casing 1 and protects them from contacting the skin 7 even if the skin attachment plate is pushed manually against the skin of the user for firmly attaching the adhesive layer 6 to the skin. Preferentially, three to four such telescopic guide ways distributed over the area of the skin attachment plate form the retraction mechanism.

FIG. 4B shows a top view of such a sliding bolt plate 26 as part of the release and actuation element. The plate has two recesses 29, each of which having a narrowed area 28 and a handle 30. The narrowed area 28 is wide enough to let the inner tube 23 of the telescopic guide ways pass through but withholds the outer tube 24, thus withholding the skin attachment plate in the ready-to-use position against the pull of the spring 25. Moving the sliding bolt plate 26 in the horizontal direction, as indicated by an arrow, by pressing the handle 30 against the casing 1 exposes holes 29 which are large enough to allow the passage of the tube 24. By this the spring 25 can relax from the pre-stressed position and the skin attachment plate 5 together with the skin 7 attached by the adhesive layer 6 is rapidly pulled against the bottom of the casing and the tip of the electrodes 3, the sensor 18 and the cannula 20, with sufficient velocity and force for piercing the skin and completely inserting the implantable portion of these elements into the skin. The resulting operational position is shown in FIG. 4C.

Upon reading these specifications, various alternative embodiments of the sub-epidermal electric warning device, of the circuitry resulting in alternating current pulses of opposite polarity, and of combinations and of assemblies or interactions with other functional elements or devices will become obvious to the skilled artisan. For example, the electric warning device could be designed to interact wirelessly with separate sensor and/or medication delivery devices. It could even be worn by a separate person than the patient being under the control of sensor systems or treated by medication delivery devices. Such a configuration might be important in cases in which the patient is not able to take himself the necessary actions upon sensing an electrical warning signal, e.g. babies or handicapped patients.

The major advantage of the sub-epidermal warning device according to the present invention compared to similar known devices is that a circuitry resulting in alternating current pulses of opposite polarity leads to better recognition at lower voltage, without rapid fading of the perceived signal and improving the window between clear comfortable signal recognition and electric shock or even pain. In addition, this device can be worn directly attached to the skin and the electrical warning signal is much less prone to become masked under unfavorable environmental conditions or during sleep compared to acoustic or vibrational signals. Penetrating through the insulating epidermis layer of the skin by placing the electrodes into the sub-epidermal tissue for delivering the electric signal directly to the sub-epidermal tissue decreases the necessary voltage and current for clear recognition to absolutely safe levels. Further, this avoids significant inter-individual and location-dependent variability and results in a great advantage for patient comfort and safety of operation.

The invention claimed is:

1. A sub-epidermal electric warning device comprising:
   electrodes to penetrate through a patient's epidermis into a skin;
   a generator of an electric warning signal which is transmitted to a sub-epidermal tissue by the electrodes, wherein an electric stimuli applied creates bipolar current pulses of alternating positive and negative polarity; and
   an inserter to provide sub-epidermal insertion of the electrodes into the skin, wherein
   the inserter is configured in such a way that in a ready-to-use position, the inserter keeps the skin away from contacting a tip of the electrodes which are fixedly positioned by a bottom of a casing of the device and, upon activation, pulls the skin towards the tip of the electrodes with a velocity to effect piercing of the skin and sub-epidermal insertion of the electrodes.

2. The sub-epidermal electric warning device according to claim 1, wherein the positive and negative pulses are following each other within 1 to 100 milliseconds and these pulse pairs follow each other in 0.2 to 5 seconds time.

3. The sub-epidermal electric warning device according to claim 1, wherein the electric warning signal is delivered with increasing intensity over time until the electric warning signal is recognized and confirmed by the patient.

4. The sub-epidermal electric warning device according to claim 3, wherein the electric warning signal is delivered with different rhythm for different warning messages.

5. The sub-epidermal electric warning device according to claim 1, wherein the generator includes control elements to generate the electric warning signal according to input signals.

6. The sub-epidermal electric warning device according to claim 5, further comprising at least one sensor system configured in such a way that when abnormal values for vital signs are measured by the at least one sensor system, the at least one sensor system transmits the input signals to the control elements to generate the electric warning signal.

7. The sub-epidermal electric warning device according to claim 6, wherein the at least one sensor system comprises subcutaneously implanted sensors to provide determination of analyte concentrations.

8. The sub-epidermal electric warning device according to claim 5, further comprising a pump system to provide subcutaneous fluid injection and configured in such a way that when functional abnormalities of the pump system occur, the pump system transmits the input signals to the control elements to generate the electric warning signal.

9. The sub-epidermal electric warning device according to claim 1, further comprising a skin attachment surface of the device coated with an adhesive layer to secure attachment to the skin.

10. The sub-epidermal electric warning device according to claim 9, wherein the adhesive layer to secure attachment to the skin is fixed on the skin attachment surface of the device by a reduced surface in comparison to a surface of the adhesive layer attached to the skin.

11. The sub-epidermal electric warning device according to claim 10, wherein the reduced surface of the adhesive layer fixed on a contact surface of the device results from a rim on the contact surface of the device to which the adhesive layer is not attached.

12. The sub-epidermal electric warning device according to claim 5, wherein the inserter comprises:
   a skin attachment surface coated with an adhesive layer to secure attachment to the skin and including holes or recesses allowing passage of the electrodes;
   a spring-type retraction mechanism of the skin attachment surface pulling the skin attachment surface together with the attached skin towards the tip of the electrodes;
   a withholder to keep the retraction mechanism pre-stressed in the ready-to-use position such that the tip of the electrodes is concealed by the skin attachment surface and prevented to contact the skin;
   a release and actuation element releasing blockage of the retraction mechanism by the withholder and actuating skin insertion of the electrodes by the relaxation of the retraction mechanism pulling the skin attached to the skin attachment surface against the tip of the electrodes, and actuating the control elements.

13. The sub-epidermal electric waning device according to claim 12, wherein the skin attachment surface is a rigid plate and the retraction mechanism is configured such that the retraction mechanism keeps the rigid plate and the bottom of the device casing parallel to each-other in the ready-to-use position and throughout retraction of the skin attachment surface towards the bottom of the device casing.

14. The sub-epidermal electric warning device according to claim 12, wherein the skin attachment surface is a flexible, segmented surface being attached to the bottom of the device casing at a periphery, and the retraction mechanism is configured such that in the ready-to-use position, the retraction mechanism stretches a central part of a contact surface away from the bottom of the device casing, forcing the skin attachment surface to form a cup or a gable.

15. The sub-epidermal electric warning device according to claim 14, wherein the retraction mechanism of the flexible, segmented surface makes use of springy elasticity of this surface to provide a rapid movement by relaxation from an enforced tense position.

16. The sub-epidermal electric warning device according to claim 1, wherein the device is composed of a reusable part comprising mainly control and additional electronic elements, and a disposable part comprising the other elements of the device.

17. A subcutaneous access device comprising the sub-epidermal electric warning device according to claim 1, wherein the sub-epidermal electric warning device is comprised in a functional package including a rim to press an outer rim of an adhesive layer towards the skin and protecting release and actuation elements of the sub-epidermal electric warning device against unintended activation.

* * * * *